United States Patent [19]
Jones et al.

[11] Patent Number: 5,672,505
[45] Date of Patent: Sep. 30, 1997

[54] INSERT FOR A ISSUE CULTURE VESSEL

[75] Inventors: Christopher L. Jones, Bloomingdale; Edward F. Mussi, Hewitt, both of N.J.

[73] Assignee: Becton, Dickinson and Company, Franklin Lakes, N.J.

[21] Appl. No.: 290,492

[22] Filed: Aug. 15, 1994

Related U.S. Application Data

[63] Continuation of Ser. No. 127,406, Sep. 27, 1993, abandoned.

[51] Int. Cl.$^6$ ............................. C12M 1/00; C12M 3/00
[52] U.S. Cl. .................. 435/283.1; 422/101; 435/297.1; 435/297.5; 435/299.2; 435/304.3
[58] Field of Search ........................... 128/759, 760; 422/101, 102; 435/284–287, 294–296, 310, 312

[56] References Cited

U.S. PATENT DOCUMENTS

| | | | |
|---|---|---|---|
| 3,740,321 | 6/1973 | Pagano et al. | 435/285 |
| 3,783,104 | 1/1974 | Henshilwood et al. | 435/295 |
| 3,834,992 | 9/1974 | Bonhke et al. | 435/296 X |
| 3,918,435 | 11/1975 | Beall et al. | 435/295 |
| 3,966,552 | 6/1976 | Pagano et al. | 435/294 |
| 4,073,695 | 2/1978 | Lyman | 435/296 X |
| 4,150,950 | 4/1979 | Takeguchi et al. | 435/295 X |
| 4,330,216 | 5/1982 | Johnson | 435/285 X |
| 4,492,305 | 1/1985 | Avery | 435/295 X |
| 4,670,396 | 6/1987 | Bear et al. | 435/285 |
| 4,865,988 | 9/1989 | Guala | 435/296 |
| 5,026,649 | 6/1991 | Lyman et al. | 435/284 |
| 5,122,470 | 6/1992 | Banes | 435/286 X |

FOREIGN PATENT DOCUMENTS

| | | | |
|---|---|---|---|
| 2-265468 | 10/1990 | Japan | 435/312 |

OTHER PUBLICATIONS

Magnum et al., In Vitro Cell Dev. Biol., 26:1135–1143 (Dec. 1990).
Madara et al. J. Tissue Cult. Method 14:209–216 (1992).

Primary Examiner—Robert J. Warden
Assistant Examiner—Arlen Soderquist
Attorney, Agent, or Firm—Arthur D. Dawson

[57] ABSTRACT

An insert of the present invention for a tissue culture bottle with a neck includes a neck adapter with provision for mounting a suspending arm. One end of the suspending arm mounts in the insert and the other end has a holder for a specimen or a plurality of specimens. When the adapter is placed in the neck of the bottle, a specimen in the holder is suspended within the bottle. The neck adapter may also be incorporated into a cap for the bottle. In the case where the tissue culture bottle is a roller bottle with a longitudinal axis, the neck adapter may include rotatable elements so that the suspending arm and specimen holder remain in a substantially constant position with respect to the rotation of the bottle about the axis. In an alternate embodiment of the insert of the present invention, the insert may be a generally cylindrical member for placement on the interior surface of a tissue culture roller bottle for at least a portion of the cell growth period. The insert of the present invention may include a vessel to be used for addition of substances or withdrawal of substances to or from a tissue culture without substantially disturbing growing cells. The insert may be used to hold porous membranes having populations of cells for co-culture with a population of ceiling in a culture bottle. The insert may include ionic exchange resin, affinity membrane, and, when the holder includes a magnet, magnetic beads with biological affinity coatings. The insert may also incorporate a sensor for monitoring pH, concentration of other ions, temperature and the like. In any of these applications, the present invention allows the practitioner to conduct the desired activity with minimal disruption to growing cells and is generally applicable to standard tissue culture bottles and other laboratory equipment.

4 Claims, 4 Drawing Sheets

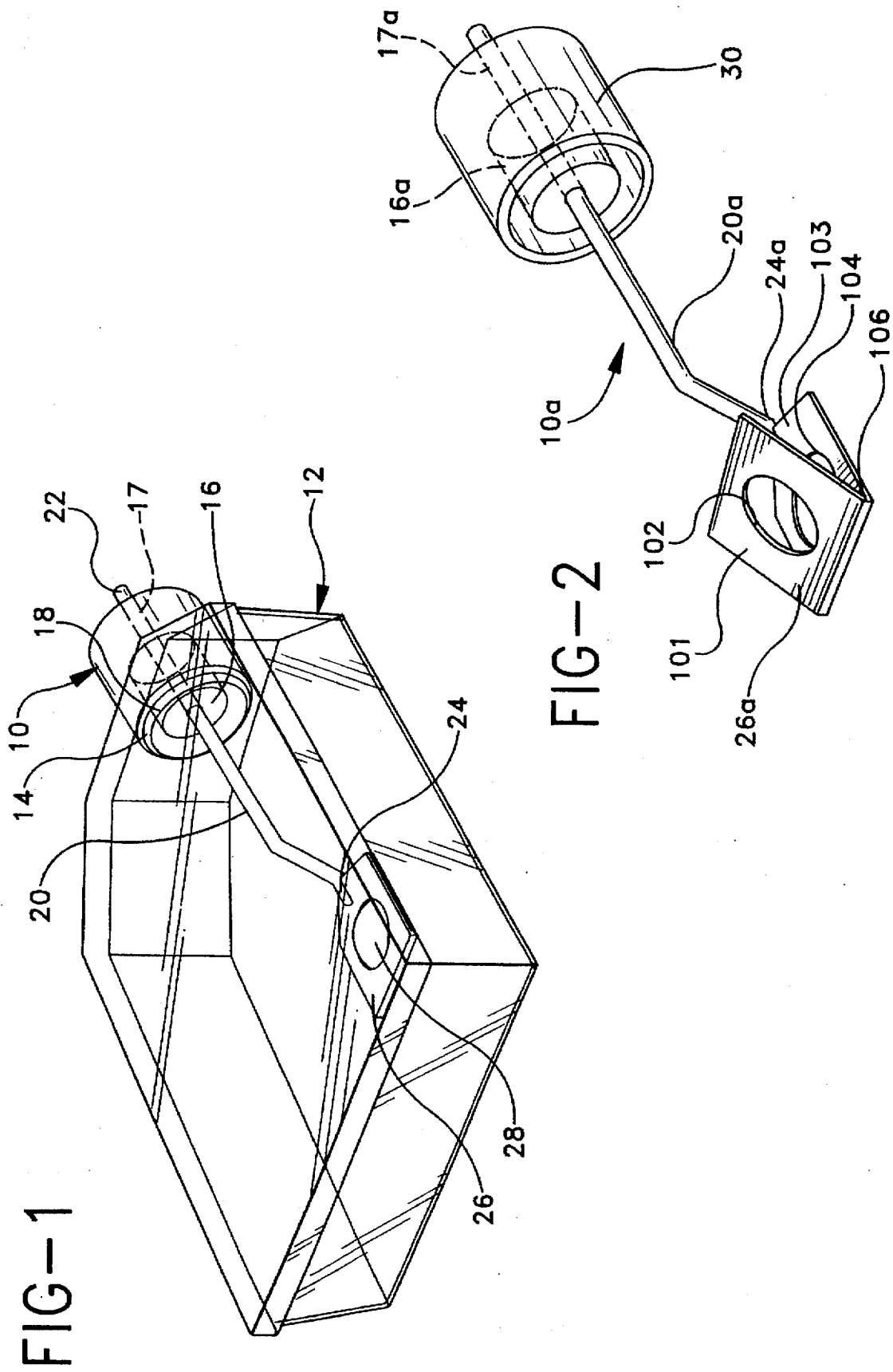

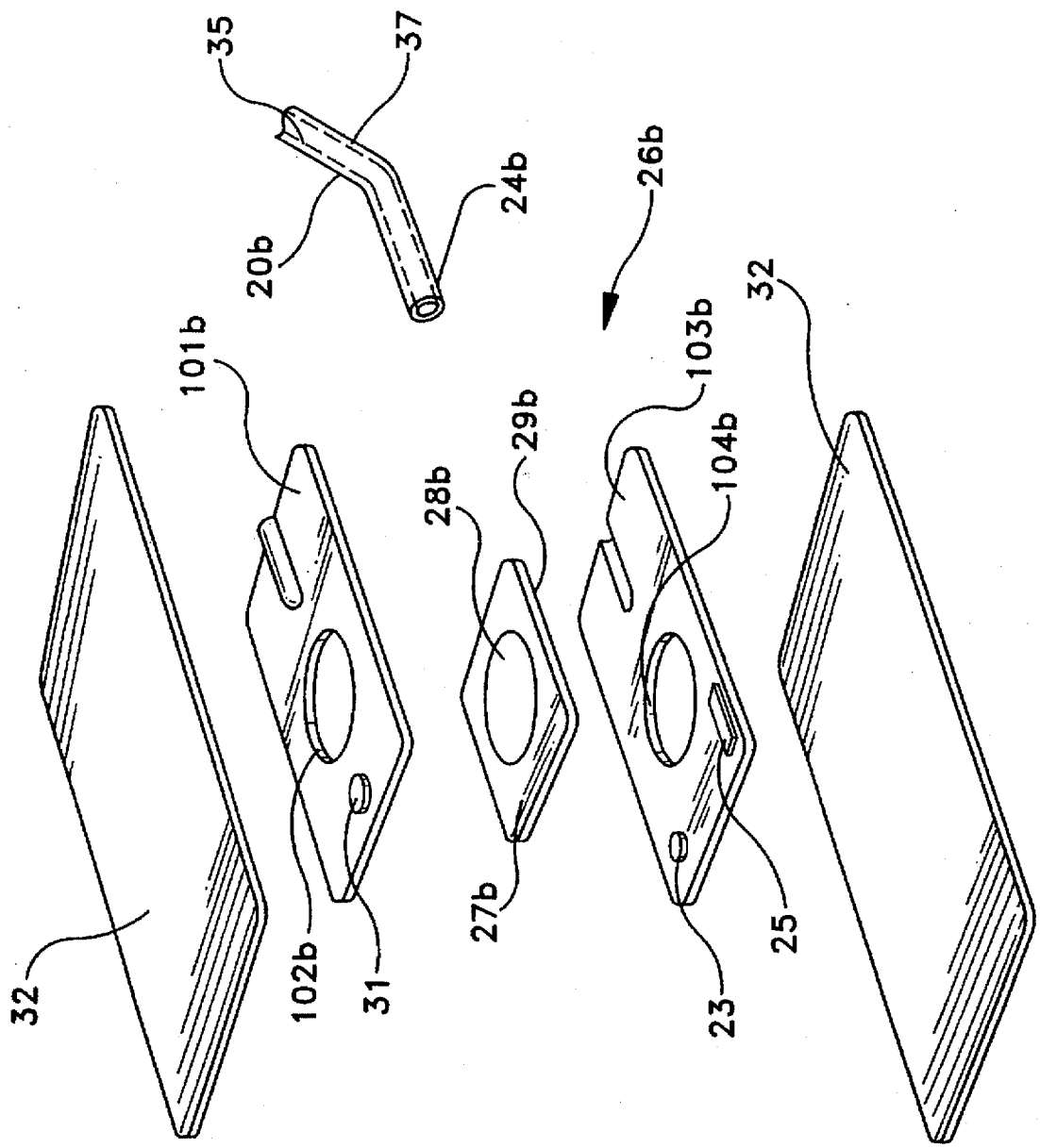

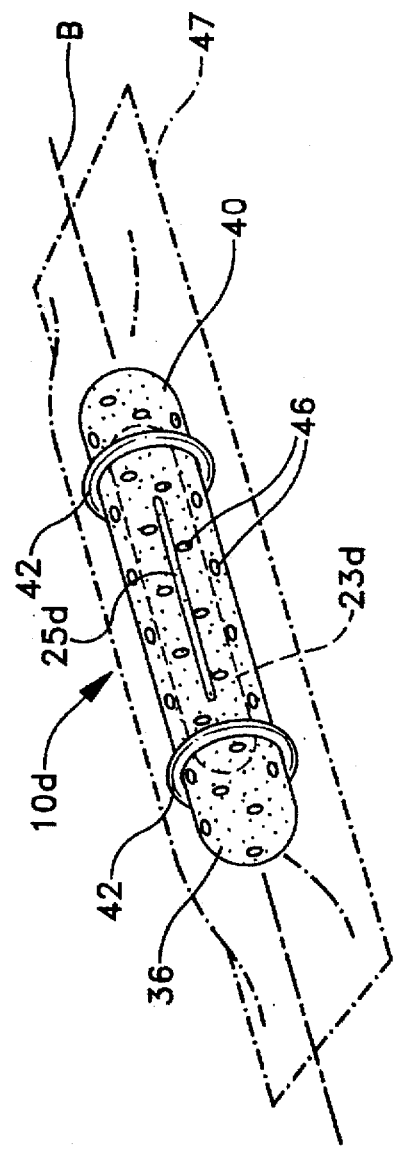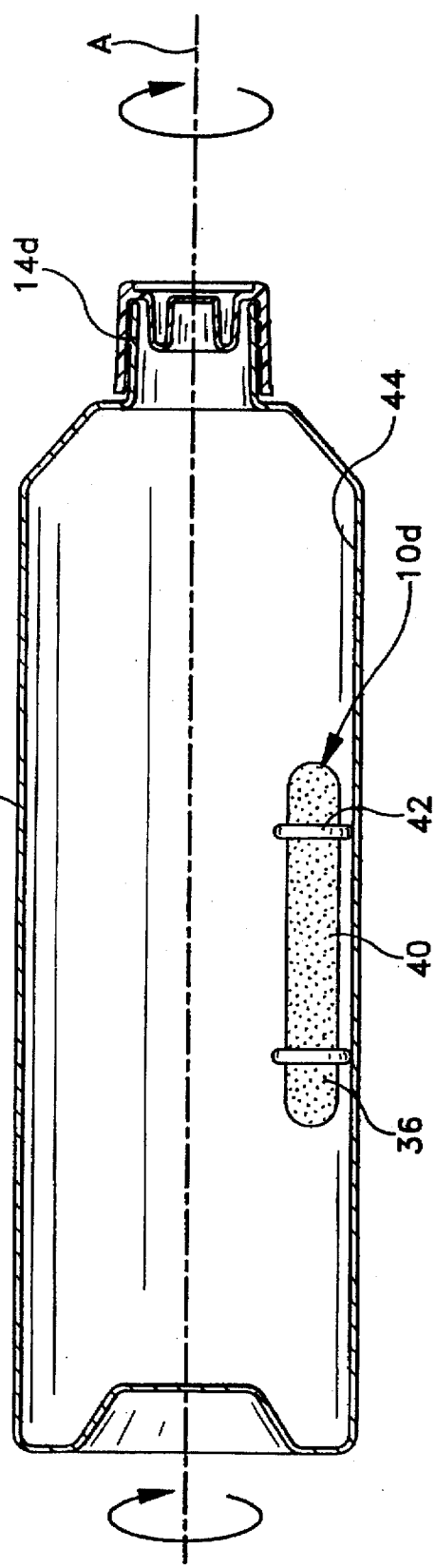

1

INSERT FOR A ISSUE CULTURE VESSEL

This application is a continuation of application Ser. No. 08/127,406, filed Sep. 27, 1993, now abandoned.

FIELD OF INVENTION

This invention relates to culturing of cells, and more particularly relates to an insert for a tissue culture bottle which allows co-culture of cells in a tissue culture bottle and addition or withdrawal of a substance to or from a tissue culture.

BACKGROUND

Culturing of cells of various types has become a routine process in many laboratories. Cells are grown to harvest compounds, test for various sensitivities to potentially toxic compounds and even to provide tissue for grafts. Tissue culture is conducted on scales ranging from multiwell micro filter plates involving only a few cells to large reactors having billions of cells.

Generally, cell culture is carded out as a monoculture. That is, cells of one particular type are grown in a suitable medium. When used as a test or diagnostic, the monoculture may be exposed to a particular substance, often by extracting the test material with the cell culture medium, then observing cells grown with the extract for adverse effects. Generally these diagnostic tests are done on a small scale.

Most recently, interest has developed in co-culture of cells. Co-culture of cells involves growing one population of cells in the presence of another population of cells. Often, the cells are grown on a porous membrane, one population on one side, one on the other side. This enables the cells to interact through chemical compounds which can pass through the membrane without having physical contact between the cells. Representative literature reports of trans-membrane co-culture studies include Magnum et al., In Vitro *Cell Dev. Biol.*, 26:1135–1143 (December, 1990) "Co-culture of primary Pulmonary Cells to Model Alveolar Injury and Translocation of Protein"; and Madara et al. in *J. Tissue Cult. Method.* 14:209–216, (1992) "A Simple Approach to Measurement of Electrical Parameters of Cultured Epithelial Monolayers: Use in Assessing Neutrophil-Epithelial Interactions." In both of these papers and the references therein, the technique of growing two populations of cells on opposite sides of a porous membrane are described. Trans-membrane co-culture of cells is useful for small scale studies, but a scale-up to the scale of two hundred seventy five milliliter fiat bottles or to the one and one half liter cylindrical roller bottles using the trans membrane techniques has not been reported. Additionally, the trans-membrane system is limited to only two cell populations, one on one side and one on the other.

In any complex organism, there are many types of cells which interact with each other. There is interest in reproducing some of these interactions more than two at one time for study of tumor growth processes; cell differentiation and other heterologous cell interaction mediated by diffusible substances. Additionally, it may be desirable to add and/or extract substances to or from a cell monoculture without disrupting the cell growth process. There may be a need to monitor temperature, pH, or other concentrations in a cell culture without disruption to the growing cells. Certain substances which are secreted only by living cells may desirably be added to a larger scale monoculture. If there is a need to maintain a physical separation between the secreting cells and the larger monoculture, there currently is no readily available system to facilitate such an addition this other than isolating the compound from a monoculture of the secreting cells and then adding it. Even if the compound were stable to the isolation conditions, the separation process adds to the time and complexity required for the monoculture.

Thus, it is apparent that the art of culturing cells could benefit from a device which would allow substances to be added or removed from a culture, provide a way to monitor the growing cells, support a multiple co-culture, or allow easy scale-up of a co-culture.

SUMMARY OF THE INVENTION

The present invention provides a simple-to-use way for a practitioner of cell culture to scale-up a co-culture. It further provides a way for a practitioner to add or remove a compound from a cell culture bottle and to monitor conditions in the bottle with minimal disturbance to the growing cells.

An insert of the present invention for a tissue culture bottle having a neck includes a neck adapter having elements for mounting a suspending arm. The suspending arm has a first end and a second end. The insert also bas elements for holding at least one specimen. The first end of the suspending arm is sized and shaped to fit the mounting elements in the neck adapter. The elements for holding a specimen are attached to the second end of the arm so that when the neck adapter is placed in the neck of the bottle, a specimen in the holder is suspended within the bottle.

In an alternate embodiment, the adapter may be incorporated into a cap for a culture bottle.

In the case where the culture bottle is a cylindrical roller bottle with a longitudinal axis, an embodiment of the present invention includes the neck adapter having rotatable elements. The rotatable elements enable the suspending arm and the holder to remain in a substantially constant position with respect to the bottle rotation. Alternate embodiments of the present invention include the specimen being a porous membrane having a substantially confluent layer of cells thereon. The holder with the cell containing membrane may then be encased in a second membrane impermeable to cells.

Additionally, an alternate embodiment of the insert of the present invention for use in a cylindrical tissue culture bottle having a longitudinal axis includes a generally cylindrical member having a longitudinal axis and having a surface encased in a substantially smooth substantially inert covering. The insert may be placed the cell culture bottle for at least a portion of a cell growth period. In this embodiment, the insert may additionally be fit with a plurality of rings placed around the member substantially perpendicular to the longitudinal axis. The rings support the insert above an inside surface of the roller bottle and substantially prevent disruption of cells by the insert movement on the inside surface of the bottle as the bottle is rotated about its longitudinal axis.

BRIEF DESCRIPTION OF THE DRAWINGS

FIG. 1 is a perspective view of a flat 275 ml tissue culture bottle having an insert of the present invention installed therein;

FIG. 2 is a schematic perspective view of an embodiment of an insert of the present invention.

FIG. 3 is an exploded perspective view of the holder portion of an embodiment of the insert of the present invention;

FIG. 5 is a perspective view of another embodiment of the insert of the present invention; and FIG. 6 is a schematic view oh roller bottle with the embodiment of the insert illustrated in FIG. 5 installed therein.

DETAILED DESCRIPTION OF THE PREFERRED EMBODIMENTS

Figure 4:
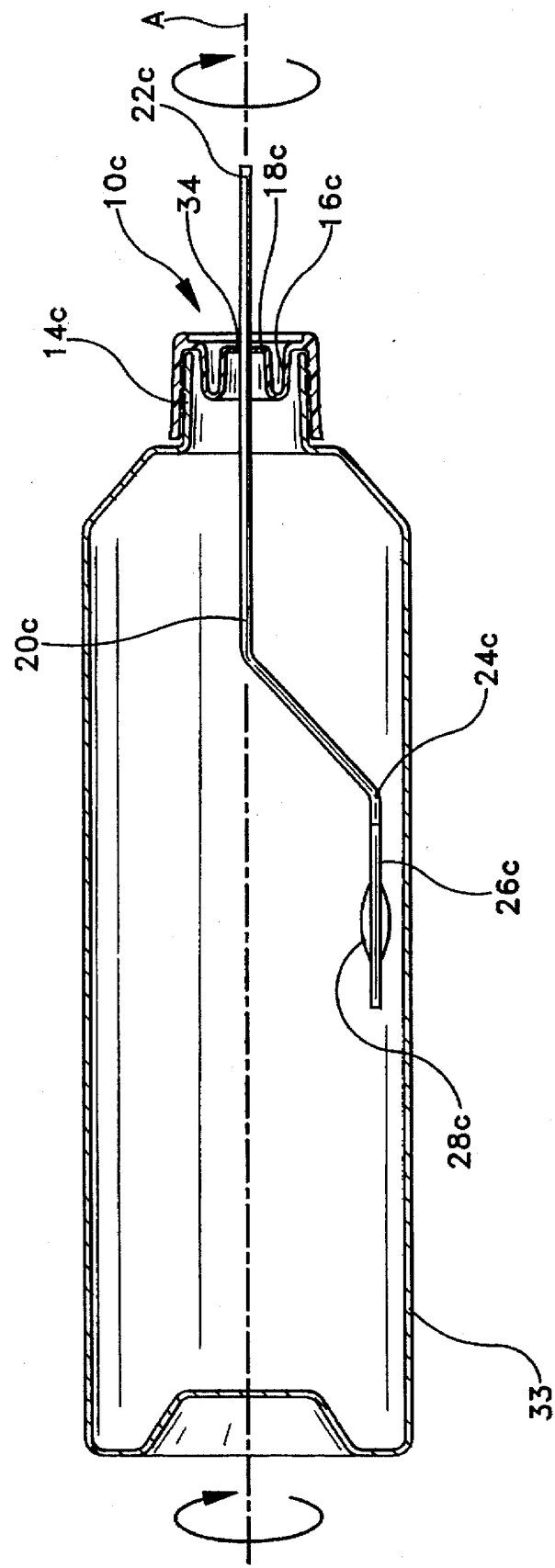
FIG. 4 is a schematic cross sectional view of an embodiment the insert of the present invention installed cell culture roller bottle.

While this invention is satisfied by embodiments in many different forms, there will be described herein in detail, preferred embodiments of the invention, with the understanding that the present disclosure is to be considered as exemplary of the principles of the invention and is not intended to limit the invention to the embodiments described. The scope of the invention will be measured by the appended claims and their equivalents.

With reference to FIG. 1 an insert 10 of the present invention for use with a tissue culture bottle 12 having a neck 14 includes a neck adapter 16 with elements 18 for mounting a suspending arm 20 having an offset 21 and having a first end 22 and a second end 24. Insert 10 also includes a specimen holder 26. First end 22 of suspending arm 20 is sized and shaped to fit mounting elements 18 in the neck adapter. Specimen holder 26 is attached at second end 24 of arm 20. Thus, a specimen 28 in holder 26 is suspended within bottle 12 when neck adapter 16 is positioned within the neck of the bottle. In many instances of tissue culture there is a need for the growing cells to be exposed to an atmosphere favorable to their growth, insert 10 may include neck adapter 16 having a passage 17 therethrough for interchange of gases and liquids.

Alternate embodiments of the present invention are shown in FIGS. 2–6. Accordingly, elements of the insert similar in structure to the insert of FIG. 1 that perform substantially similar functions will be numbered identically to those components of the embodiment of FIG. 1 except that suffixes will be used to identify similar components.

Adverting to FIG. 2, an alternate embodiment of insert 10a has neck adapter 16a incorporated into a cap 30 for a tissue culture bottle. Specimen holder 26a preferably includes an upper portion 101 having a passageway 102 therethrough an a lower portion 103 having a passageway 104 therethrough. In this embodiment preferably lower portion 103 is attached to arm 20a with offset 21a at second end 24a. Upper portion 101 preferably is attached to lower portion 103 at attachment 106 opposite second end 24. Attachment 106 may simply be a flex point in specimen holder 26a as shown in FIG. 2 or may include any other simple fastener so that the specimen is held between upper portion 101 and lower portion 103 so that at least a portion of the specimen is exposed in the passageways. The actual method of attachment is not critical. Incorporation of the adapter directly into a cap for a roller bottle simplifies the usage and assembly of the insert into the bottle.

FIG. 3 shows an exploded detail of an embodiment of insert 10b. Arm 20b with offset 21b has specimen holder 26b at second end 24b. Specimen holder 26b preferably includes an upper potion 101b having a passageway 102b therethrough and a lower portion 103b having a passageway 104b therethrough. Preferably lower portion 103b is attached to arm 20b at second end 24b. Upper portion 101b preferably is attached to lower portion 103b. Attachment 106 may simply be a flex point in specimen holder 26a as shown in FIG. 2 or may include any other simple fastener so that the specimen is held between upper portion 101b and lower portion 103b so that at least a portion of the specimen is exposed in the passageways. The actual method of attachment is not critical. The specimen may be a porous membrane having a population of cells thereon which is then substantially sealed within a second membrane 32. Membrane 32 may also be impermeable to cells and serves to isolate the cells of specimen 28b from cells present in the culture bottle.

Specimen 28b may include a porous membrane having a top side 27b and a bottom side 29b for culturing cells with a substantially confluent layer of initial cells on the top side and a substantially confluent layer of second cells on the bottom side with each side substantially sealed by membrane 32b substantially impermeable to cells. Holder 26b may further include provisions for mounting a plurality of porous membranes having cell populations, each isolated from the bulk culture and each other by a second membrane impermeable to cells.

Holder 26b may include a magnet 23 in second portion 103b to facilitate attachment of magnetic particles to the holder having a coating of biologically active molecules bonded thereto for conducting affinity separations of binding materials. Suitable biomagnetic particles are available as Biomag® from Collaborative Research Bedford, Mass.

Holder 26b may include an affinity membrane which allows selective passage of material into or out of the contents of the culture bottle. Holder 26b may further include at least one vessel 25 for containing and releasing a substance which is desired to be added to the contents of the culture bottle during cell growth. The holder may also incorporate resin having ion exchange properties for withdrawal or release of a substance into the cell culture bottle.

It additionally would be possible to incorporate at least one transducer 31 into holder 26b and at least one conductor 35 into arm 24b for communicating a signal with the transducer. The transducer could be used to monitor pH, other ionic concentrations, temperature and the like in the cell culture bottle. Arm 24b may further include at least one tube 37 with a passageway therethrough to add or withdraw components to or from the cell culture.

FIG. 4 illustrates an alternate embodiment of insert 10c mounted in a tissue culture roller bottle 33. Bottle 33 is generally cylindrical, has a longitudinal axis "A" and has a coaxial neck 14c. Insert 10c includes a neck adapter 16c sized to fit neck 14c of the bottle. The insert further includes suspending arm 20c having a first end 22c and a second end 24c. Neck adapter 16c incorporates a mount 18c having rotatable elements 34 for receiving first end 22c of arm 20c. The insert includes a holder 26c at second end 24c of the arm for holding at least one specimen 28c. When first end 22c is mounted at mount 18c having rotatable elements 34 and bottle 33 is horizontally rotated about axis "A", holder 26c and arm 24c are suspended within the bottle in a substantially constant location with respect to the rotation about the bottle axis.

The particular material from which the insert of the present invention is formed is not essential to the present invention, but preferably includes polymeric resins such as polystyrene, polyvinyl chloride, polycarbonate and the like known to have compatibility with the cell culture medium and which is not toxic to cells.

An alternate embodiment of the insert 10d of the present invention is shown in FIGS. 5 and 6. Insert 10d for a tissue culture roller bottle 33d having an axis "A" includes a generally cylindrical member 36 having a longitudinal axis "B" and a surface 38 having a substantially smooth, substantially inert coating 40. Insert 10d is placed in bottle 33d and the bottle is rotated about axis "A". Insert 10d may further include a plurality of rings 42 placed about member 36 substantially perpendicular to axis "B" to support the insert above an inside surface 44 of bottle 32d and substantially prevent disruption of cells growing on surface 44 as the bottle is rotated about axis "A".

Insert 10d may incorporate a magnet 23d so that magnetic beads 46 with a biologically active coating will adhere to surface 38 of the member. Additionally, insert 10d may be encased in a membrane 47 impermeable to cells so that compounds may be transmitted or withdrawn from the cell culture medium without withdrawal of cells. Insert 10d may also include a vessel 25d for containing and releasing a substance into the tissue culture bottle. The vessel may additionally incorporate ionic exchange resin.

The insert of the present invention provides the cell culture art with an ability to scale-up a co-culture using existing equipment and further, allows monitoring, addition to and withdraw from tissue cultures without substantial disruption to the growing cells.

What is claimed is:

1. An insert for a tissue culture bottle having a neck comprising:

a neck adapter having mounting means sized to fit the neck of the bottle;

a suspending arm having a first end and a second end, said arm having an offset intermediate said first end and said second end;

holder means for holding at least one specimen, said specimen including a porous first membrane having cells thereon, substantially sealed within a second porous membrane impermeable to cells; and said first end of said suspending arm being sized and shaped to fit said mounting means for suspending said suspending arm into the bottle from said first end, said holder means being attached at said second end of said suspending arm, so that a specimen in said holder is suspended within the bottle when said neck adapter is placed in the neck of the bottle.

2. The insert of claim 1 wherein said first membrane has a substantially confluent layer of initial cells on a top side and a substantially confluent layer of second cells on a bottom side, each additionally separately being substantially sealed within a porous cover membrane substantially impermeable to cells.

3. An insert for a tissue culture bottle having a neck comprising:

a neck adapter having mounting means sized to fit the neck of the bottle;

a suspending arm having a first end and a second end and having an offset intermediate said first end and said second end;

holder means for holding at least one specimen, said holder means comprising an upper portion having a passageway therethrough and a lower portion having a passageway therethrough, said lower portion being attached at said second end of said suspending arm and said upper portion being attached to said lower portion, said specimen being held between said upper portion and said lower portion so that at least a portion of said specimen is exposed by said passageways; and said first end of said suspending arm being sized and shaped to fit said mounting means for suspending said suspending arm into the bottle from said first end, said holder means being attached at said second end of said suspending arm, so that a specimen in said holder is suspended within the bottle when said neck adapter is placed in the neck of the bottle.

4. The insert of claim 3 wherein said specimen is selected from the group consisting of at least one membrane having a top side and a bottom side for culturing cells.

* * * * *

UNITED STATES PATENT AND TRADEMARK OFFICE
CERTIFICATE OF CORRECTION

PATENT NO. : 5,672,505
DATED : September 30, 1997
INVENTOR(S) : Christopher L. Jones et al.

It is certified that error appears in the above-identified patent and that said Letters Patent is hereby corrected as shown below:

On the title page, item [54] and Column 1, line 1, should read as follows:

——INSERT FOR A TISSUE CULTURE VESSEL——

Signed and Sealed this

Twenty-second Day of September, 1998

Attest:

BRUCE LEHMAN

Attesting Officer

Commissioner of Patents and Trademarks